United States Patent [19]
Ace

[11] 3,949,756
[45] Apr. 13, 1976

[54] SUTURES WITH NOTCH NEAR NEEDLE-SUTURE JUNCTION

[75] Inventor: Franklin S. Ace, Oldwick, N.J.
[73] Assignee: Ethicon, Inc., Somerville, N.J.
[22] Filed: Nov. 20, 1974
[21] Appl. No.: 525,328

[52] U.S. Cl. .................. 128/339; 163/1; 223/102
[51] Int. Cl.² ...................................... A61B 17/06
[58] Field of Search ......... 128/335.5, 339; 163/1.5; 223/102

[56] References Cited
UNITED STATES PATENTS

| | | | |
|---|---|---|---|
| 1,665,216 | 4/1928 | Morton et al. | 128/339 |
| 3,320,954 | 5/1967 | Cowley | 128/218 N |
| 3,799,169 | 3/1974 | Beroff et al. | 128/339 |
| 3,875,946 | 4/1975 | Duncan | 128/339 |

*Primary Examiner*—Dalton L. Truluck
*Attorney, Agent, or Firm*—Wayne R. Eberhardt

[57] ABSTRACT

A needle-suture combination is provided in which the suture has a weakened segment adjacent its attachment to the needle. The weakened segment is provided by a notch which reduces the effective cross-sectional area of the suture by a controlled amount. The weakened segment permits a surgeon to separate the needle from the suture by a sharp tug.

11 Claims, 6 Drawing Figures

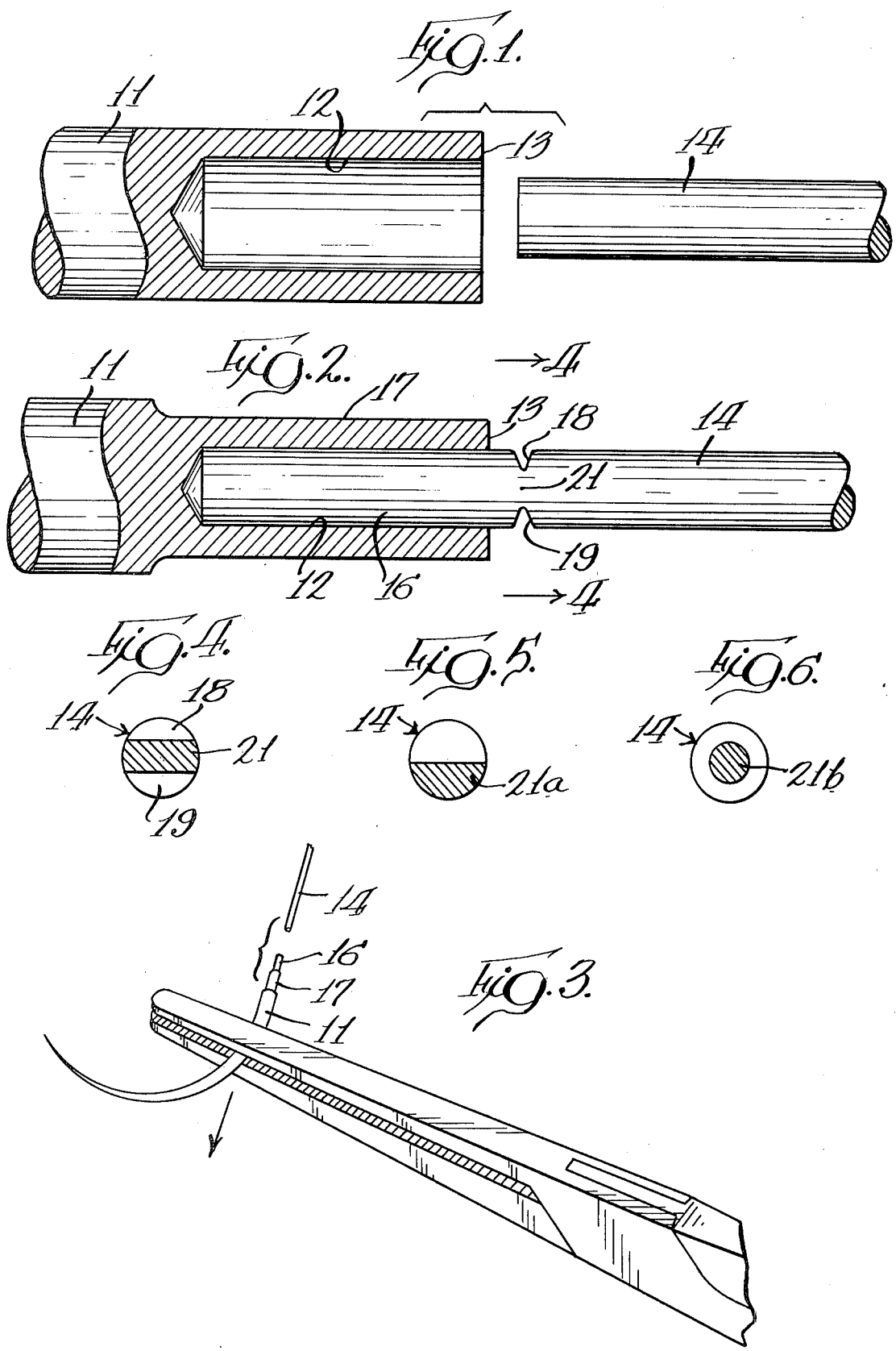

SUTURES WITH NOTCH NEAR NEEDLE-SUTURE JUNCTION

BACKGROUND OF THE INVENTION

This invention relates to needle-suture combinations and particularly to a combination of a surgical needle with a suture in which the force necessary to separate the needle from the suture is within an acceptable range for convenient removal of the needle from the suture by a sharp tug.

In many surgical procedures, surgeons use a technique which employs a non-needled suture and an eyed needle. The needle is threaded by the nurse and the surgeon takes one pass through the tissue using a needleholder. He slips the needle off the suture, returns the needle to the nurse, and is ready for another threaded needle from the nurse. An assistant follows behind and ties the suture.

Some surgeons find that this technique is more simple than using a needled item and cutting the suture with a scissors after each pass. However, the time required for threading results in a significant waste of expensive operating room time.

The security of attachment of eyeless needles to absorbable surgical sutures or to non-absorbable surgical sutures is prescribed in the *U.S. Pharmacopoeia*, Vol. XVIII at Page 944 (also see *U.S. Pharmacopoeia*, Vol. XVII, Page 919). It has been the practice of suture manufacturers in the United States and abroad to securely attach the suture to the needle by swaging or with an adhesive so that the minimum pull-out standard recited in the *U.S. Pharmacopoeia* is met or exceeded.

To avoid the problems discussed above it has been found useful to use needle-suture combinations in which the needle and the suture are readily separable from each other by a sharp tug. Several methods have been devised for preparing needle-suture combinations in which the pull-out values, or the force required for separating the needle from the suture by a straight pull, is within a controlled range.

One approach to the problem is described in co-pending and co-assigned application Ser. No. 409,974, filed Oct. 26, 1973. This approach involves inserting into a drilled hole in the blunt end of the needle one end of a braided suture which has been sized with a resin and is smaller in diameter than the remainder of the suture and then swaging the needle at its blunt end to provide a controlled degree of compression to the end of the suture within the hole. This approach is particularly useful for needle-suture combinations wherein the suture is of large size, i.e., size 4-0 and larger (diameter greater than 7.0 mils), and produces average pull-out values of 3 to 26 ounces, indicating that it takes a straight pull of a magnitude within that range to separate the needle from the suture.

Another approach to the problem is described in co-pending and co-assigned application Ser. No. 446,174, filed by Robert Barclay Duncan on Feb. 27, 1974. In this approach sufficient tension is applied to the suture in a swaged needle-suture combination to move the suture relative to the needle recess and the tension is released when the force drops to the range desired for the pull-out value, the range varying for different sizes of suture. This approach is applicable to a broad range of suture sizes, including sizes as small as 8-0.

The present invention provides another approach to the problem and provides for easy separation of needles from needle-suture combinations without requiring any change in the manner of manufacture of the needlesuture combinations. It also permits the conversion of existing stocks of needle-suture combinations to products from which the needles can be separated by application of moderate force.

BRIEF SUMMARY OF THE INVENTION

In accordance with the present invention there is provided a needle-suture combination comprising a needle having a sharp end and a blunt end and having a recess at said blunt end, a suture having one tip positioned within said recess, means retaining said tip of said suture within said recess to attach said suture to said needle, and a weakened segment in said suture adjacent the location of its attachment to said needle, the weakened segment being produced by the notching of the suture in the desired location to a controlled degree.

Notching of the suture at the desired location is obtained by application of at least one cutting edge thereto or by application of at least one abrasive surface to the suture surface at the desired location with relative movement between the abrasive and suture surfaces.

In one preferred embodiment a notching device is used which has two parallel blades facing each other and firmly set with a measured gap between them. As the suture is moved transversely to the blade direction, two straight notches are formed, facing each other with a preset width of unnotched suture between them.

In another embodiment the needle-suture combination is held within a groove and against the bed thereof; and a knife-edge is moved transversely into the area of the groove with a stroke that is restricted by a stop so that a desired distance is maintained between the bed of the groove and the end of the knife stroke whereby a single notch is formed on one side of the suture and a controlled portion of the suture on the opposite side remains uncut, or unnotched.

In other embodiments the notching is achieved in a similar manner except that a pair of rotating abrasive wheels or a single rotating abrasive wheel is used in place of the knife edges, or knife edge.

Other embodiments provide for notching about the periphery of the suture by rotating the suture in contact with a knife-edge, or with a grinding wheel until a circumferential notch of the desired depth is formed.

The sutures suitable for use in the preparation of the notched needle-suture combination of this invention include both monofilaments and multifilament structures such as braided, twisted and covered sutures. Suitable suture materials include collagen (including catgut and extruded collagen), silk, cotton, linen and synthetic polymers, including nylon, polypropylene and polyesters, such as polyethylene terephthalate, and homopolymers and copolymers of lactide and glycolide.

When the sutures are notched in accordance with this invention, it has been found that the remaining strength of the suture is less than would be expected if the strength and cross-sectional areas were directly proportional. Usually, the rupture strength of the suture at the notched segment is only about 1/2.5 to about 1/2.0 times the rupture strength that would be expected based on the relative areas of the original suture cross section and the cross section of the unnotched portion of the suture at the location of the notch or notches.

With multifilament sutures, the entire cross-sectional area of the suture is not made up of suture material since there is, of necessity, some free space between the suture strands. The proportion of the total cross-sectional area of a suture which is occupied by the suture strands is called "suture density" and generally runs in braided sutures, for example, from about 0.70 to about 0.95, and most usually from about 0.80 to about 0.92.

The suture densities of braided structures and suture densities in general are calculated from the volume of the sample of the suture and the volume of the fiber therein in accordance with the formula:

$$D = \frac{F}{S}$$

in which $S$ is the volume of the suture, $F$ is the volume of the fiber, and $D$ is the suture density.

For convenience, it is best to determine volumes in samples at fixed lengths of 9,000 meters, of $9 \times 10^5$ centimeters. This is convenient because fiber denier is defined as weight in grams per 9,000 meters. At this length, the volume of the suture in cubic centimeters is:

$$\frac{\pi d^2 (9 \times 10^5)}{4}$$

where $d$ is the diameter of the suture in centimeters. The volume in cubic centimeters of the individual fibers, $F$, at the same length would be:

$$\frac{(\text{number of strands})(\text{denier per strand})}{r}$$

or $$\frac{\text{denier of suture}}{r}$$

where $r$ is the density of the suture material in grams per cubic centimeter. The load at which a notched suture will rupture may be estimated from the equation:

$$P = \frac{ATD}{K}$$

wherein $P$ is the rupture load, in pounds;
$T$ is the tensile strength of the suture material, in pounds per square inch;
$A$ is the area, in square inches, remaining unnotched at the notched portion of the suture;
$D$ is the suture density of the suture, being unity in the case of a monofilament; and
$K$ is a constant factor, initially determined empirically for each suture material and represents the degree of weakening at the notched portion of the suture over and above the weakening to be expected from its reduced area. As a useful approximation, $K$ may be taken at values in the range of 2.0 to 2.5 for natural and synthetic polymeric suture materials.

The unnotched area required to obtain a desired level of rupture strength at a notched portion of a suture may be calculated from another form of the same equation:

$$A = \frac{KP}{DT}$$

in which $A$, $K$, $P$, $D$, and $T$ are as defined above.

It is usually desired that the suture be rupturable at its notched portion by a force of from about 3 ounces to about 26 ounces, or from about 0.2 to about 1.6 pounds, and these limits may be inserted in the above equation as the limiting values for $P$. Selecting an average $P$ value of 0.8 provides leeway for differences in individual sutures and for differences in their notching and assures rupture strengths within the desired range for most of the notched sutures. In some instances, it may be desirable to unify that portion of a multifilament structure to be notched in order to prevent fraying or brooming of the cut ends. By "unification" it is meant that the treated portion of the suture is transformed from a collection of loose, individual filaments to a single, coherent structure. Unification of multifilament suture tips is commonly employed in the prior art to prevent brooming of cut ends and to facilitate needle attachment. Such unification may be accomplished by any of several methods such as by impregnating the suture with a resin or other binder, or by fusing the individual filaments by the application of heat or solvent. Unification by resin treatment is described in above referenced U.S. application Ser. No. 409,974, which application is hereby incorporated by reference.

BRIEF DESCRIPTION OF THE DRAWINGS

The invention will become more readily apparent upon consideration of the following detailed description when taken in connection with the accompanying drawings wherein:

FIG. 1 is an enlarged elevation, partly in cross section of the blunt end of the needle and the suture end to be inserted therein;

FIG. 2 is an enlarged elevation, partly in cross section of the needle-suture juncture of one aspect of this invention after the suture is inserted into the blunt end of the needle, the blunt end is swaged and two diametrically opposed notches are cut into the suture adjacent to juncture to the needle;

FIG. 3 is a perspective view of the needlesuture combination of the present invention as the needle is separated from the suture after use and during the surgical procedure;

FIG. 4 is a cross-sectional view at plane 4—4 of FIG. 2;

FIG. 5 is a cross-sectional view similar to FIG. 4, but illustrating another embodiment of the invention; and FIG. 6 is a cross-sectional view similar to FIGS. 4 and 5, but illustrating another embodiment of the invention.

DETAILED DESCRIPTION

As may be seen in FIG. 1, needle 11 has a cylindrical hole 12 drilled into its blunt end 13, the hole being of a somewhat larger transverse dimension than suture 14 so that one end of the suture can be inserted into the hole.

FIG. 2 shows that suture end 16 has been inserted into the hole and that cold pressure has produced swaged portion 17 at the blunt end of the needle, reducing the transverse dimension of the hole and gripping suture end 16 tightly. Suture 14 has been partially cut to produce diametrically opposed notches 18 and 19 at a location close to the juncture of the surface and the needle, leaving a residual cross-sectional area 21, as shown in FIG. 4.

In an alternative embodiment, the notch may be cut into one side of the suture, leaving a residual cross-sectional area 21a, as shown in FIG. 5.

In still another embodiment, the suture may be cut peripherally to produce a circumferential notch and leave a centrally located, circular residual cross-sectional area 21b, as shown in FIG. 6.

EXAMPLES 1 to 10

A suture notcher was arranged with a pair of blades facing each other at a distance of 0.0025 inches. A group of 10 size 0 chromic gut sutures (0.0189 inches average diameter) were passed transversely between the blades to cut opposed notches into the sutures, leaving an approximately rectangular unnotched cross-sectional area measuring 0.0189 inches by 0.0025 inches.

The notching and the subsequent rupture tests in these examples and in other examples involving gut sutures were performed on the sutures directly after removal from the package and while the sutures were still wet with tubing fluid.

The tensile strength of chromic gut varies between 45,000 psi and 65,000 psi and averages 55,000 psi.

From the above equation, and the average tensile strength value, and at a K factor of 2.5, the predicted rupture strength is 1.04 pounds, or 16.7 ounces. The actual rupture strengths for the 10 sutures were:

| Example | Rupture Strength (ounces) | (Grams) |
|---|---|---|
| 1 | 28 | 794 |
| 2 | 20 | 567 |
| 3 | 12 | 340 |
| 4 | 10 | 284 |
| 5 | 28 | 794 |
| 6 | 26 | 737 |
| 7 | 12 | 340 |
| 8 | 19 | 539 |
| 9 | 20 | 567 |
| 10 | 16 | 454 |
| Average | 19.1 ounces | 541 grams |

EXAMPLES 11 to 19

The procedure of Examples 1 to 10 was repeated with nine samples of size 3-0 chromic gut having an average diameter of 0.0122 inches.

From the above equation, using the same average tensile strength for the suture material and the same K factor, the predicted rupture strength is 0.67 pounds, or 10.7 ounces. The actual rupture strengths for the sutures were:

| Example | Rupture Strength (ounces) | (Grams) |
|---|---|---|
| 11 | 17 | 482 |
| 12 | 6 | 170 |
| 13 | 14 | 394 |
| 14 | 11 | 312 |
| 15 | 9 | 255 |
| 16 | 7 | 198 |
| 17 | 8 | 227 |
| 18 | 4 | 113 |
| 19 | 10 | 284 |
| Average | 9.6 ounces | 272 grams |

EXAMPLES 20 to 47

The procedure of Examples 1 to 19 was repeated with 12 samples of size 0 braided silk sutures and with 16 samples of size 3-0 braided silk sutures.

The average diameter of the size 0 sutures was 0.015 inches and the average diameter of the size 3-0 sutures was 0.0092 inches. The average suture density for braided silk sutures is about 0.90 for size 0, and about 0.92 for size 3-0. The average tensile strength of silk is approximately 60,000 psi.

From these values, and using the above equation and a K factor of 2.0, the predicted rupture strength at the notched zone of the size 0 sutures is about 1.01 pounds, or about 16.2 ounces; and that of the size 3-0 sutures is about 0.64 pounds, or about 10.3 ounces. The actual values were as follows:

| | Example | Rupture Strength (ounces) | (Grams) |
|---|---|---|---|
| Size O Silk | 20 | 14 | 397 |
| | 21 | 29 | 822 |
| | 22 | 17 | 482 |
| | 23 | 5 | 142 |
| | 24 | 3 | 85 |
| | 25 | 15 | 425 |
| | 26 | 7 | 198 |
| | 27 | 23 | 652 |
| | 28 | 12 | 340 |
| | 29 | 12 | 340 |
| | 30 | 3 | 85 |
| | 31 | 16 | 454 |
| | Average | 13 ounces | 369 grams |

| | Example | Rupture Strength (ounces) | (Grams) |
|---|---|---|---|
| Size 3-0 Silk | 32 | 10 | 284 |
| | 33 | 6 | 170 |
| | 34 | 18 | 510 |
| | 35 | 14 | 397 |
| | 36 | 8 | 227 |
| | 37 | 18 | 510 |
| | 38 | 18 | 510 |
| | 39 | 19 | 539 |
| | 40 | 6 | 170 |
| | 41 | 24 | 680 |
| | 42 | 23 | 652 |
| | 43 | 15 | 425 |
| | 44 | 11 | 312 |
| | 45 | 13 | 369 |
| | 46 | 12 | 340 |
| | 47 | 14 | 397 |
| | Average | 14 ounces | 397 grams |

The invention has been described with respect to preferred embodiments but other embodiments and modifications will be apparent to those skilled in the art.

What is claimed is:

1. A needle-suture combination comprising a needle having a sharp end and a blunt end and having a recess at said blunt end, a suture having one tip positioned within said recess, means retaining said tip of said suture within said recess to attach said suture to said needle, and a weakened segment in said suture adjacent the location of its attachment to said needle and exterior of said recess, said weakened segment having a breaking strength of from about 3 to 26 ounces and comprising a notch in said segment which reduces the cross-sectional area at said segment to a value (in square inches) equivalent to $KP/DT$ in which $K$ is a constant factor ranging from about 2.0 to about 2.5, $P$ is a rupture load value between about 0.3 and 1.6 pounds, $D$ is the suture density of the suture, and $T$ is the tensile strength of the suture material in pounds per square inch, whereby said needle can readily be separated from said suture by applying a pulling force to said needle to break said weakened segment.

2. The needle-suture combination of claim 1 wherein said suture comprises a monofilament and said suture density is unity.

3. The needle-suture combination of claim 1 wherein said suture comprises a braided suture and said suture density is between about 0.70 and about 0.95.

4. The needle suture combination of claim 1 wherein said suture comprises a synthetic polymeric material selected from the group consisting of nylon, polyester, and polypropylene.

5. The needle-suture combination of claim 4 wherein said suture comprises a polyester selected from the group consisting of polyethylene terephthalate and homopolymers and copolymers of glycolide and lactide.

6. The needle-suture combination of claim 1 wherein said suture comprises a material selected from the group consisting of collagen, silk, cotton, and linen.

7. The needle-suture combination of claim 1 wherein said notch extends about the entire periphery of said suture.

8. The needle-suture combination of claim 1 wherein said notch extends inwardly into said suture from one side thereof.

9. A method of altering a needle-suture combination in which a needle is attached to a suture which comprises weakening a segment of said suture located adjacent to and exterior of the needle to reduce the breaking strength of said segment to about 3 to 26 ounces by notching said segment to the extent that the cross-sectional area of said suture at the location of said notch is at a value (in square inches) equivalent to $KP/DT$ in which $K$ is a constant factor ranging from about 2.0 to about 2.5, $P$ is a rupture load value between about 0.3 and 1.6 pounds, $D$ is the suture density of the suture, and $T$ is the tensile strength of the suture material in pounds per square inch, whereby said needle can readily be separated from said suture by applying a pulling force to said needle to break said weakened segment.

10. The method of claim 9 wherein said segment is notched by a cutting action.

11. The method of claim 9 wherein said segment is notched by grinding.

* * * * *